US012778993B2

(12) United States Patent
Mao et al.

(10) Patent No.: US 12,778,993 B2
(45) Date of Patent: Nov. 3, 2026

(54) BIFIDOBACTERIUM ANIMALIS IN ENRICHING ORGANIC ZINC TO PROMOTE GROWTH AND REPRODUCTIVE DEVELOPMENT

(71) Applicant: Jiangnan University, Wuxi (CN)

(72) Inventors: Bingyong Mao, Wuxi (CN); Shumao Cui, Wuxi (CN); Xinran Han, Wuxi (CN); Xin Tang, Wuxi (CN); Qiuxiang Zhang, Wuxi (CN); Jianxin Zhao, Wuxi (CN); Wei Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 232 days.

(21) Appl. No.: 18/650,203

(22) Filed: Apr. 30, 2024

(65) Prior Publication Data

US 2024/0277784 A1 Aug. 22, 2024

Related U.S. Application Data

(63) Continuation of application No. PCT/CN2023/079598, filed on Mar. 3, 2023.

(30) Foreign Application Priority Data

Mar. 3, 2022 (CN) ......................... 202210203177.6

(51) Int. Cl.

| | |
|---|---|
| ***C12N 1/00*** | (2006.01) |
| ***A61K 35/745*** | (2015.01) |
| ***A61P 3/02*** | (2006.01) |
| ***C12N 1/205*** | (2026.01) |
| ***C12N 1/38*** | (2006.01) |
| *C12R 1/01* | (2006.01) |

(52) U.S. Cl.

CPC .............. *A61K 35/745* (2013.01); *A61P 3/02* (2018.01); *C12N 1/205* (2021.05); *C12N 1/38* (2013.01); *C12R 2001/01* (2021.05)

(58) Field of Classification Search

CPC combination set(s) only.
See application file for complete search history.

(56) References Cited

U.S. PATENT DOCUMENTS

2010/0203018 A1 8/2010 Benedetti et al.

FOREIGN PATENT DOCUMENTS

| | | | |
|---|---|---|---|
| CN | 101971921 | A | 2/2011 |
| CN | 108220208 | A | 6/2018 |
| CN | 108841763 | A | 11/2018 |
| CN | 112251366 | A | 1/2021 |
| CN | 114574387 | A | 6/2022 |
| JP | 2000279164 | A | 10/2000 |
| WO | 2008117302 | A1 | 10/2008 |

*Primary Examiner* — Jennifer E Graser
(74) *Attorney, Agent, or Firm* — IPro, PLLC; Na Xu

(57) ABSTRACT

The present disclosure discloses a strain of highly organic zinc-enriched *Bifidobacterium animalis* capable of promoting growth and reproductive development, belonging to the technical field of microorganisms. The *B. animalis* CCFM1230 screened by the present disclosure can efficiently enrich inorganic zinc and convert same into organic zinc, which is better absorbed and utilized by organisms, and effectively promotes growth and reproductive development. Animal experiments have proved that zinc-rich *B. animalis* can promote the growth and reproductive development of male rat pups, exert higher biological activity than inorganic zinc, and meet the physiological requirements of zinc supplementation. According to the present disclosure, the *B. animalis* CCFM1230 can efficiently enrich inorganic zinc for the preparation of a probiotic preparation capable of promoting growth and reproductive development, and thus has great application prospects in the field of food or medicine.

15 Claims, 2 Drawing Sheets

BIFIDOBACTERIUM ANIMALIS IN ENRICHING ORGANIC ZINC TO PROMOTE GROWTH AND REPRODUCTIVE DEVELOPMENT

TECHNICAL FIELD

The present disclosure relates to a strain of highly organic zinc-enriched *Bifidobacterium animalis* capable of promoting growth and reproductive development, belonging to the technical field of microorganisms.

BACKGROUND

Zinc is a trace element necessary to maintain normal growth and development of the human body. The human body contains 2-3 g of zinc, nearly 90% of which is found in muscles and bones. Healthy adults get about 10-15 mg of zinc daily from their diet, with a typical absorption rate of 20-30%. Zinc deficiency is considered to be a widespread nutritional deficiency worldwide, affecting approximately 31% of the global population, and is prevalent in both developed and developing countries, especially in developing countries. Zinc deficiency will lead to growth retardation and hypogonadism. Mild to moderate zinc deficiency is common all over the world. At present, in some poverty-stricken areas of China, due to the low intake of animal-based food, the access to zinc-rich food is limited, and plant-based food is the main food after birth. Phytate in the vegetable diet will inhibit the absorption of zinc, resulting in long-term zinc deficiency during growth and development, and further affecting growth and development.

Due to the inability of zinc to be stored in the human body, it is necessary to supplement zinc daily to maintain the normal functioning of the body, which may easily cause zinc deficiency in the human body. Zinc supplementation is currently mainly achieved through the additional intake of products containing organic or inorganic zinc. There are three types of zinc supplements on the market: inorganic zinc (ZnO, $ZnSO_4$, $ZnCl_2$, etc.), simple organic zinc (zinc gluconate, zinc acetate, zinc propionate, etc.), and organic zinc (amino acid chelated zinc, protein complexed zinc, etc.). Different zinc supplements have different absorption efficiencies. Studies have shown that organic zinc is more easily absorbed by the human body than inorganic zinc. The absorption rate of inorganic zinc is low, and the side effects thereof are obvious. The absorption rate of organic zinc alone is higher than that of inorganic zinc, but there are still some side effects such as gastrointestinal stimulation. Organic zinc is mainly synthesized artificially, which is relatively safe, but is more complicated in synthesis.

Microbial enrichment of zinc has been a research hotspot in recent decades. Adding inorganic salts to media enables microorganisms to enrich mineral ions, enrich trace elements on the cell surfaces or transport same into cells for storage. They exist in a form of complexes with amino acids, proteins, lipids and polysaccharides, thus realizing the transformation of inorganic trace elements into organic trace elements, and providing a good dietary source for the human body to supplement organic trace elements. At present, most of the strains used to enrich zinc by microorganisms are yeasts, and bifidobacteria are rarely used. In contrast, there are few reports on zinc-rich bifidobacteria, while bifidobacteria, as a common and beneficial microorganism to human health, also have the function of enriching metal ions. Moreover, bifidobacteria have more probiotic properties, and enriching zinc with bifidobacteria may have higher value than enriching zinc with yeasts. Zinc-rich probiotics can also regulate intestinal microbiota while supplementing zinc. As a new type of dietary zinc source containing active probiotics, the zinc-rich probiotics have more advantages than probiotics or other zinc supplements, which is worth exploring. Compared to supplementing inorganic zinc alone, it is necessary to study efficiently enriching inorganic zinc with the zinc-rich probiotics and converting same into organic zinc, and develop a zinc supplement that is inexpensive, simple to prepare, safe and reliable, and more efficient in supplementing zinc.

SUMMARY

The present disclosure provides a probiotic preparation. The probiotic preparation contains *B. animalis* CCFM1230 or a product of the *B. animalis* CCFM1230 subjected to zinc enrichment culture; and the *B. animalis* CCFM1230 has been preserved in Guangdong Microbial Culture Collection Center (GDMCC) on Feb. 11, 2022, with a preservation number of GDMCC No: 62248.

In one embodiment, the product obtained after zinc enrichment culture includes cells from the *B. animalis* CCFM1230 subjected to zinc enrichment culture, or cell lysates containing organic zinc obtained from the *B. animalis* CCFM1230 subjected to zinc enrichment culture.

In one embodiment, the *B. animalis* CCFM1230 has the following characteristics:

(1) The strain is present as small, white and opaque colonies after being cultured on an MRS medium for 48 h; and (2) inorganic zinc can be efficiently enriched and converted into organic zinc, which can be better absorbed and utilized by organisms.

In one embodiment, the cells include, but are not limited to living cells or dead cells.

In one embodiment, the dead cells include, but are not limited to naturally inactive cells or inactivated cells.

In one embodiment, the probiotic preparation per gram or per milliliter contains the $\geq 1\times10^{10}$ CFU/g or $\geq 1\times10^{10}$ CFU/mL *B. animalis* CCFM1230, or cells obtained after zinc enrichment culture.

In one embodiment, the zinc enrichment culture is to culture the *B. animalis* CCFM1230 in a zinc-rich medium until the number of bacterial cells is greater than or equal to $1\times10^{8}$ CFU/mL.

In one embodiment, the zinc enrichment culture is to culture the *B. animalis* CCFM1230 in the zinc-rich medium for a period of time; and the zinc ion concentration in the zinc-rich medium is 200-700 mg/L.

In one embodiment, after being subjected to zinc enrichment culture, the *B. animalis* CCFM1230 is also subjected to drying process; and the drying process includes but is not limited to: vacuum freeze drying, spray drying, vacuum drying or fluidized bed drying.

The present disclosure further provides a preparation method of zinc-enriched *B. animalis* CCFM1230. The method includes the following steps:

(1) streaking the *B. animalis* on a modified MRS solid medium, and culturing upside down by a streak plate method at 37° C. for 36-48 h; picking single colonies and inoculating same into a modified MRS liquid medium, and culturing at 37° C. for 24 h; then, inoculating the cultured product into a modified MRS liquid medium at an inoculation amount of 2% (v/v), and culturing at 37° C. for 12-18 h as seed bacterial liquid for subsequent culture;

(2) inoculating the seed bacterial liquid of the *B. animalis* into a zinc-rich liquid medium at an inoculation amount of 2% (v/v), and culturing for 12-18 h; and (3) after the fermentation is completed, centrifuging the bacterial liquid at 8000 g for 20 min at 4° C., and rinsing the wet bacterial cells 2 times with pure water to obtain the bacterial slurry of the zinc-enriched *B. animalis*.

In one embodiment, the zinc ion concentration in the zinc-rich liquid medium in step (2) is 200-700 mg/L.

In one embodiment, the zinc-rich liquid medium contains: 20-30 g/L glucose, a 15-25 g/L nitrogen source (a mass ratio of yeast extract powder to peptone is 1:2), 2 g/L anhydrous sodium acetate, 2 g/L diammonium hydrogen citrate, 2.6 g/L $K_2HPO_4 \cdot H_2O$, 0.1 g/L $MgSO_4 \cdot 7H_2O$, 0.05 g/L $MnSO_4 \cdot H_2O$, 1 g/L Tween-80, 0.5 g/L cysteine, and zinc sulfate (added according to the conversion of zinc ion concentration from 200 to 700 mg/L).

In one embodiment, the bacterial slurry of the zinc-enriched *B. animalis* is also subjected to drying process, so that bacterial powder of highly organic zinc-enriched *B. animalis* is obtained.

In one embodiment, the bacterial slurry of the zinc-enriched *B. animalis* is also arbitrarily subjected to drying process; and the drying process includes but is not limited to spray drying, vacuum drying, fluidized bed drying, or vacuum freeze drying.

In one embodiment, the bacterial slurry of the zinc-enriched *B. animalis* is inactivated and then arbitrarily subjected to drying process to obtain bacterial powder of highly organic zinc-enriched *B. animalis* CCFM1230 without cellular activity; and the drying process uses protein or dextrin as a filling agent, or does not use any filling agent.

The present disclosure also provides application of the *B. animalis* CCFM1230 or the probiotic preparation in the preparation of products capable of promoting the growth and reproductive development of young mammals.

In one embodiment, the products include food, medicines or health care products.

Beneficial Effects

The present disclosure provides a strain of highly organic zinc-enriched *B. animalis*, which can enrich and absorb inorganic zinc and convert same into biological zinc in bacteria. After the strain is subjected to zinc enrichment culture, the zinc content in bacterial powder per gram can reach 3.8 mg or above, and the organic zinc content can reach 95.3%. The number of viable cells in the bacterial powder can reach $4.73 \times 10^9$ CFU/g or above. Regardless of whether having activity or not, the organic zinc enriched by the strain can be better absorbed and utilized by organisms, which can effectively promote the growth and reproductive development of mammals.

Biological Material Preservation

The *B. animalis* CCFM1230, classified and named *Bifidobacterium animalis*, has been preserved in Guangdong Microbial Culture Collection Center (GDMCC) on Feb. 11, 2022, with a preservation number of GDMCC No: 62248. The preservation address is 5$^{th}$ floor, Building 59, No. 100, Xianlie Middle Road, Guangzhou.

DETAILED DESCRIPTION

Figure 1:
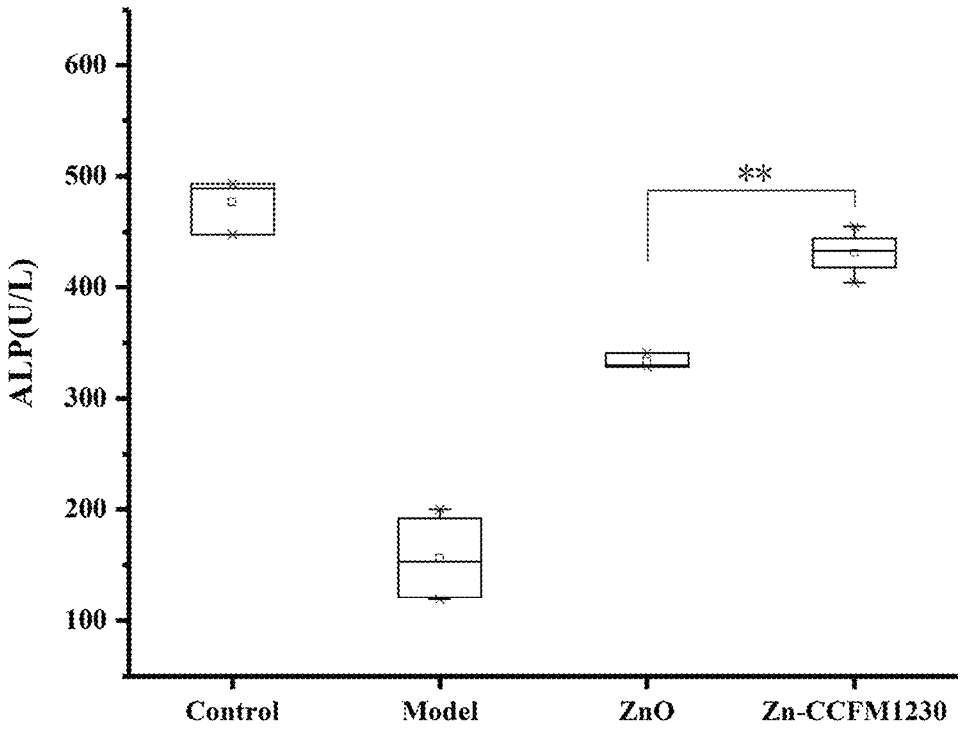
FIG. 1 shows the effect of zinc supplementation on ALP activity in rat serum; Note: different symbols represent significant differences between groups (*p<0.05, p<0.01)
Figure 2:
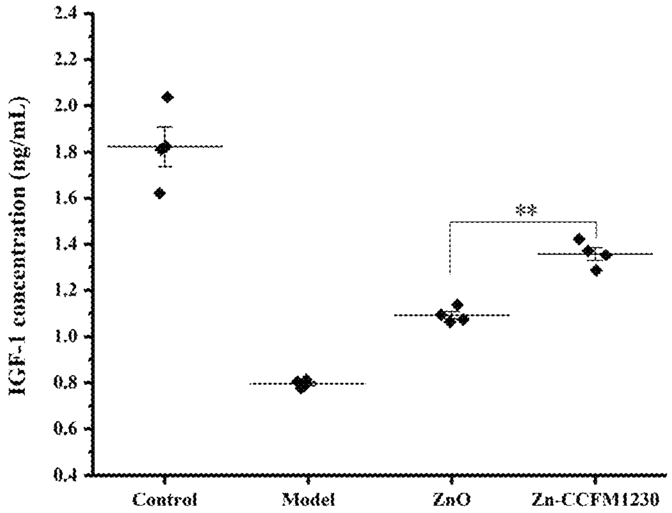
FIG. 2** shows the effect of zinc supplementation on the concentration of insulin-like growth factor and testosterone in rat serum; Note: different symbols represent significant differences between groups (*p<0.05, **p<0.01).
Figure 2:
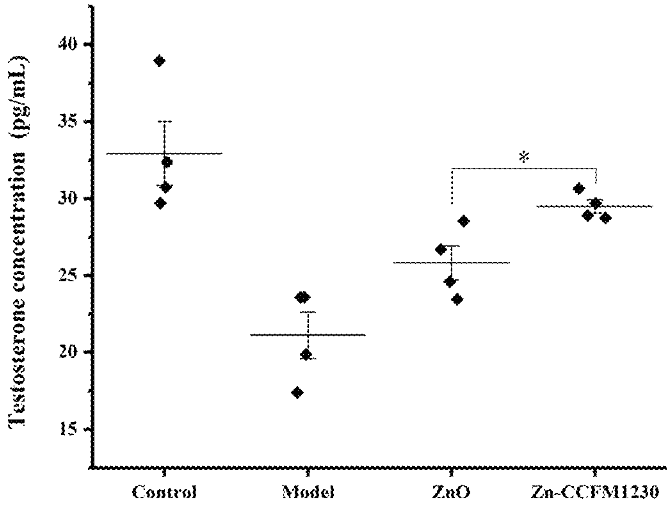

The present disclosure will be further elaborated below in conjunction with specific examples.

Zinc sulfate (product code: 10024018, CAS: 7446-20-0) involved in the following examples was purchased from Sinopharm Chemical Reagent Co., Ltd.; and nitric acid (product code: yb2-308, CAS: 7697-37-2) was purchased from Sinopharm Chemical Reagent Co., Ltd.

Media Involved in the Following Examples are as Follows

Modified MRS liquid medium: 10 g/L peptone, 10 g/L beef extract, a 5 g/L yeast extract, 20 g/L glucose, 2 g/L anhydrous sodium acetate, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4 \cdot H_2O$, 1 g/L Tween-80, 0.5 g/L cysteine, and 1000 g/L distilled water.

Modified MRS solid medium: 10 g/L peptone, 10 g/L beef extract, a 5 g/L yeast extract, 20 g/L glucose, 2 g/L anhydrous sodium acetate, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4 \cdot H_2O$, 1 g/L Tween-80, 0.5 g/L cysteine, 20 g/L agar, and 1000 g/L distilled water.

Zinc-rich liquid medium: 20-30 g/L glucose, a 15-25 g/L nitrogen source (a mass ratio of yeast extract powder to peptone was 1:2), 2 g/L anhydrous sodium acetate, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4 \cdot H_2O$, 1 g/L Tween-80, 0.5 g/L cysteine, 1000 g/L distilled water, and zinc sulfate (added according to the conversion of zinc ion concentration from 200 to 700 mg/L).

Example 1: Screening, Strain Identification, and Preservation of *B. animalis*

1. Screening

Infant feces from Shanghai were taken as samples, and 10-fold gradient dilution was carried out with sterile normal saline until the samples were diluted to $10^{-6}$; after that, 100 μL of dilution solutions with dilution factors of $10^{-4}$, $10^{-5}$ and $10^{-6}$ were respectively taken and coated on a modified MRS solid medium by a spread plate method, and then were cultured at 37° C. for 48 h; and colony morphology was observed and recorded. Colonies of different morphologies on the modified MRS solid medium were selected for streaking isolation; and after the colonies were cultured at 37° C. for 48 h, single colonies of different morphologies on the modified MRS solid medium were selected again for streaking isolation until the pure single colonies of consistent morphologies were obtained. The pure colonies on the modified MRS solid medium were selected and inoculated into a zinc-rich liquid medium containing zinc sulfate, and then were cultured at 37° C. for 18 h; the bacterial liquid was transferred to a sterile centrifuge tube, and centrifuged at 8000 g for 10 min; and the superstratum medium was discarded, and the obtained bacterial slurry was rinsed for 2 times and then freeze-dried to obtain zinc-rich bacterial powder. An atomic absorption spectrophotometer was used to detect the zinc content in the bacterial powder, and the strains with stronger zinc enrichment ability were selected.

2. Identification

The isolated strain with stronger zinc enrichment ability was subjected to PCR amplification of 16S rDNA, and the PCR product was sent to Invitrogen Trading (SHANGHAI) Co., Ltd. for sequencing. The sequencing results were compared with nucleic acid sequences in NCBI, and finally a strain of *B. animalis* was obtained, named *Bifidobacterium animalis* CCFM1230.

3. Preservation

The *B. animalis* CCFM1230 was inoculated into a modified MRS liquid medium and cultured at 37° C. for 18 h; 1 mL of bacterial liquid was taken into a sterile centrifuge tube, centrifuged at 8000 g for 10 min, and then the superstratum medium was discarded; and the bacterial slurry was resuspended in a 30% glycerol solution and preserved at −80° C.

Example 2 Preparation Method of Zinc-Enriched *B. animalis*

(1) The *B. animalis* CCFM1230 screened in Example 1 was streaked on a modified MRS solid medium, and cultured upside down by a streak plate method at 37° C. for 48 h; single colonies were picked and inoculated into an MRS liquid medium, and cultured at 37° C. for 24 h; and then, the cultured product was inoculated into a modified MRS liquid medium at an inoculation amount of 2% (v/v), and cultured at 37° C. for 12-18 h as seed bacterial liquid for subsequent culture.

(2) The seed bacterial liquid obtained in step (1) was inoculated into a fermentation flask containing a zinc-rich liquid medium at an inoculation amount of 2% (v/v), and cultured for 12-18 h.

(3) The bacterial liquid obtained after the fermentation in step (2) was centrifuged at 8000 g for 20 min at 4° C., and the wet bacterial cells were rinsed for 2 times with pure water; skimmed milk with mass fraction of 13% was used as a freeze-dried protective agent, the washed wet bacterial cells and the freeze-dried protective agent were mixed well at a mass ratio of 1:1, and freeze-dried to obtain bacterial powder of highly zinc-enriched *B. animalis*, with the number of viable cells being $4.73\times10^9$ CFU/g; and the content of organic zinc in the bacterial powder per gram can reach 3605.45 μg or above.

Optionally, bacterial powder may also be prepared by inactivating and drying the zinc-enriched *B. animalis*, and the drying method may be selected from spray drying, vacuum drying, fluidized bed drying, or vacuum freeze drying.

Optionally, the bacterial powder of the inactivated highly zinc-enriched *B. animalis* can be prepared according to the following method: after the fermentation of the aforementioned step (2) was completed, the bacterial liquid was centrifuged at 8000 g for 20 min at 4° C., the wet bacterial cells were rinsed for 2 times with pure water, and the washed wet bacterial cells were subjected to spray drying, vacuum drying, fluidized bed drying, or vacuum freeze drying; protein or dextrin was used as a filling agent (the mass ratio of bacterial slurry to a filling agent solution was 1:1, and the filling agent solution was whey protein, collagen, soybean protein, or a dextrin solution with a mass fraction of 13%); and the bacterial powder of the inactive highly zinc-enriched *B. animalis* was obtained, and the content of organic zinc in the bacterial powder per gram can reach 3605.45 μg or above.

TABLE 1

| Bacterial powder of zinc-enriched *B. animalis* CCFM1230 | | |
|---|---|---|
| Zinc ion concentration (mg/L) | Zinc content (mg/g) | Organic zinc content (mg/g) |
| 200 | 3.78042 | 3.60545 |
| 300 | 4.09433 | 3.88552 |
| 400 | 9.28867 | 8.84281 |
| 500 | 23.39082 | 22.17450 |
| 600 | 54.41239 | 51.74618 |
| 700 | 103.56302 | 98.38487 |

Example 3: Detection of Zinc Content and Organic Zinc in Zinc-Enriched *B. animalis*

1. Detection of Zinc Content in Zinc-Enriched *B. animalis*

(1) Microwave Digestion

Referring to the method in Example 2, bacterial liquid of *B. animalis* CCFM1230 was obtained by fermentation in a zinc-rich liquid medium with zinc ion concentration of 200 mg/L, and bacterial powder thereof was prepared. 0.1 g-0.15 g of a bacterial powder sample was weighed and put into a microwave digestion tank, and 5 mL of nitric acid was added for microwave digestion. After cooling, the digestion tank was taken out, and the acid was removed on an electric heating plate at 140° C.-160° C. until being about 1 mL. After the digestion tank was cooled off, a digestion solution was transferred to a 25 mL volumetric flask, the digestion tank was washed 2-3 times with a small amount of water, a washing solution was combined into the volumetric flask, the volume was set to scale by using water, and the obtained product was mixed well for later use. At the same time, a reagent blank test was carried out.

(2) Preparation of Standard Solution

① Standard zinc stock solution (1000 mg/L): 1.2447 g (accurate to 0.0001 g) of zinc oxide was accurately weighed, a small amount of nitric acid solution with a volume fraction of 50% was added, the mixture was heated for dissolving, and then cooled and transferred into a 1000 mL volumetric flask, water was added to scale, and the obtained product was mixed evenly.

② Standard zinc intermediate solution (10 mg/L): 0.5 mL of the standard zinc stock solution (1000 mg/L) was accurately pipetted and put into a 50 mL volumetric flask, a nitric acid solution with a volume fraction of 5% was added to scale, and the obtained product was mixed evenly.

③ Standard Zinc series solutions: 0 mL, 0.5 mL, 1 mL, 2 mL, 4 mL, and 5 mL of the standard zinc intermediate solution were accurately pipetted and put into a 50 mL volumetric flask, respectively; and a nitric acid solution with a volume fraction of 5% was added to scale, and the obtained products were mixed evenly. The mass concentrations of the standard zinc series solutions were 0 mg/L, 0.1 mg/L, 0.2 mg/L, 0.4 mg/L, 0.8 mg/L and 1 mg/L, respectively.

The zinc content in the sample was measured by flame atomic absorption spectrometry with reference to the first method in the national standard GB 5009.14-2017 of the People's Republic of China, and the detection result was 3.8 mg/g.

2. Analysis on Organic Zinc in Zinc-Enriched *B. animalis*

0.5 g of bacterial powder of zinc-enriched *B. animalis* CCFM1230 was accurately weighed and put into a beaker, 45 mL of distilled water was added, and the pH of the distilled water was adjusted to 6.5 with dilute acid or alkali.

After that, a 50 mL volumetric flask was used to determine the volume, and the pH of the distilled water with the determined volume was adjusted to 6.5. After the volume was determined, a zinc-enriched *B. animalis* solution was transferred to a beaker, and then slowly and uniformly stirred with a glass rod for 5-10 min. After stirring, the solution was centrifuged at 8000 g for 15 min at room temperature. The supernatant obtained by centrifugation was collected for measuring the water-soluble zinc (i.e., inorganic zinc) content on the cell surfaces of the zinc-enriched *B. animalis.* 45 mL of a 10 mmol/L EDTA solution was added into the precipitate, and the pH of the EDTA solution was adjusted to 6.5 with dilute acid or alkali. After that, a 50 mL volumetric flask was used to determine the volume, and the pH of the EDTA solution with the determined volume was adjusted to 6.5. After the volume was determined, a zinc-enriched *B. animalis* solution was transferred to a beaker, and then slowly and uniformly stirred with a glass rod for 5-10 min. After stirring, the solution was centrifuged at 8000 g for 15 min at room temperature. The supernatant obtained by centrifugation was collected for measuring the content of zinc complexed by cell wall polysaccharides and proteins. The second centrifugation precipitation was used to measure the contents of organic macromolecules or small molecules bound to zinc in the cells of the zinc-enriched *B. animalis.*

Organification degree=(content of zinc complexed by cell wall polysaccharides and proteins+content of organic macromolecules or small molecules bound to zinc in cells)/total zinc content The zinc content in each component was measured by flame atomic absorption spectrometry with reference to the first method in the national standard GB 5009.14-2017 of the People's Republic of China. The detection results are as follows:

TABLE 2

Analysis on zinc content in bacterial powder of zinc-enriched *B. animalis* CCFM1230

| CCFM1230 | Inorganic zinc | Cell wall complexed zinc | Intracellular bound zinc | Total zinc content |
|---|---|---|---|---|
| Zinc content (μg/g) | 179.33 | 303.75 | 3301.70 | 3784.79 |
| Percentage (%) | 4.74 | 8.03 | 87.24 | 100 |

It can be seen that the total zinc content of the bacterial powder of the zinc-enriched *B. animalis* CCFM1230 reaches 3.8 mg/g, indicating that the *B. animalis* has a stronger ability to enrich zinc. The content of inorganic zinc is 4.7%, indicating that the assimilation effect of the *B. animalis* on the inorganic zinc is better. 8.0% of zinc is bound to macromolecules such as polysaccharides and proteins in the cell wall in a form of organisms; and 87.2% of zinc is bound to organic macromolecules or small molecules in the cells of the *B. animalis*. The same method was used to detect the organic zinc content in the bacterial powder of the inactive highly zinc-enriched *B. animalis*. The results show that the total zinc content in the bacterial powder prepared from the inactivated bacterial slurry is 3.8 mg/g, the inorganic zinc content is 4.7%, and the organic zinc content is 95.3%.

Comparative Example 1: Zinc Enrichment Amounts and Organification Degrees of Different Zinc-Enriched *B. animalis*

The zinc content of probiotics from different sources after zinc enrichment culture was retrieved and collected, where *Bifidobacterium bifidum* O4, *Bifidobacterium adolescentis* W5, *Bifidobacterium adolescentis* HuNan-2016 MRS 11-2, *Bifidobacterium animalis* HuNan-2016 22-3, *Bifidobacterium breve* HuNan-2016 49-7, *Bifidobacterium breve* GuXi-2016 6-7, *Lactobacillus reuteri* 138-1, and *Lactobacillus bulgaricus* MJ-1 were published in the paper Enrichment Characteristics of Lactic Acid Bacteria for Zinc and Relieving Effect of Zinc-rich Lactic Acid Bacteria on Colitis in Mice; *Bifidobacterium breve* WC 0421, *Bifidobacterium breve* WC 0480, *Bifidobacterium breve* WC 0481, *Bifidobacterium infantis* WC 0460, and *Bifidobacterium pseudocatenulatum* WC 0455 were published in the paper Zinc Uptake by Lactic Acid Bacteria; and *Bacillus subtilis* NZ56 was published in the patent with Publication No. CN 108220208 B.

TABLE 3

Comparison of zinc contents of different zinc-enriched bifidobacteria

| Strain preservation number | Latin name | Zinc content (mg/g) |
|---|---|---|
| CCFM1230 | *B. animalis* | 3.78 |
| O4 | *B. bifidum* | 0.26 |
| W5 | *B. adolescentis* | 0.39 |
| HuNan-2016 MRS 11-2 | *B. adolescentis* | 0.20 |
| HuNan-2016 22-3 | *B. animalis* | 0.22 |
| HuNan-2016 49-7 | *B. breve* | 0.18 |
| GuXi-2016 6-7 | *B. breve* | 0.064 |
| WC 0421 | *B. breve* | 2.08 |
| WC 0480 | *B. breve* | 0.975 |
| WC 0481 | *B. breve* | 1.105 |
| WC 0460 | *B. infantis* | 2.08 |
| WC 0455 | *B. pseudocatenulatum* | 2.015 |
| NZ56 | *Bacillus subtilis* | 2.512 |

The strains shown in Table 3 were cultured in the same manner as in Example 2, and the zinc content after 18 h of culture was measured. *Bifidobacterium breve* F-JS-ZJ-1-M5, *Lactobacillus rhamnosus* DG11-1, *Lactobacillus plantarum* NFM11, *Lactobacillus casei* RS-2-1, *Lactobacillus fermentium* NT65-2 were the zinc-enriched strains obtained by self-screening.

TABLE 4

Comparison of organification degrees of different zinc-enriched bifidobacteria

| Strain | | Zinc content (μg/g) Inorganic zinc | Cell wall complexed zinc | Intracellular bound zinc | Total zinc content | Organification degree |
|---|---|---|---|---|---|---|
| CCFM1230 | *B. animalis* | 179.33 | 303.75 | 3301.70 | 3784.79 | 95.3% |
| O4 | *B. bifidum* | 22.62 | 25.05 | 193.49 | 241.15 | 90.6% |

TABLE 4-continued

Comparison of organification degrees of different zinc-enriched bifidobacteria

| Strain | | Zinc content (μg/g) Inorganic zinc | Cell wall complexed zinc | Intracellular bound zinc | Total zinc content | Organification degree |
|---|---|---|---|---|---|---|
| W5 | *B. adolescentis* | 33.26 | 50.04 | 311.09 | 394.38 | 91.6% |
| F-JS-ZJ-1-M5 | *B. breve* | 55.81 | 61.95 | 607.20 | 724.96 | 92.3% |
| DG11-1 | *L. rhamnosus* | 90.53 | 62.95 | 666.67 | 820.15 | 89.0% |
| 138-1 | *L. reuteri* | 69.25 | 25.22 | 344.26 | 438.73 | 84.2% |
| NFM11 | *L. plantarum* | 53.56 | 23.35 | 290.73 | 367.65 | 85.4% |
| RS-2-1 | *L. casei* | 55.38 | 17.89 | 200.90 | 274.17 | 79.8% |
| NT65-2 | *L. fermentium* | 85.07 | 28.37 | 479.29 | 592.73 | 85.6% |
| MJ-1 | *L. bulgaricus* | 42.53 | 21.90 | 185.38 | 249.81 | 82.9% |

The above are the strains described in the existing documents or patents, which are relatively low in zinc enrichment content and organic zinc conversion rate, and thus cannot achieve the desired effects of high zinc enrichment and high organic zinc content of the strain provided by the present disclosure.

Example 4: The Effect of Zinc-Enriched *Bifidobacterium longum* on the Growth and Reproductive Development of Male Rat Pups 1. Modeling: Twenty 3-week-old male SD rat pups were selected and randomly divided into 4 groups: normal group, zinc-deficient group, inorganic zinc group, and zinc-enriched *B. animalis* group, with 5 rats in each group. The rats of the zinc deficiency group, the inorganic zinc group, and the zinc-enriched *B. animalis* group were fed with zinc-deficient feed TP0690-01G (1 ppm) (ordered from Nantong Trophic Animal Feed High-tech Co., Ltd.) for one week for zinc-deficiency modeling, and the rats in the normal group were fed with control feed.

2. Intervention: From the 2$^{nd}$ week, intragastric administration was carried out at a gavage volume of 1.0 mL.

The rats in the inorganic zinc group were gavaged with zinc oxide suspension daily at a dose of 0.7 mg of Zn/rat while being fed with zinc-deficient feed;

the rats in the zinc-enriched *B. animalis* group were gavaged with bacterial suspension daily at a dose of 0.7 mg of Zn/rat while being fed with zinc-deficient feed (the bacterial powder prepared in Example 2 according to the zinc content was dissolved in normal saline);

the rats in zinc-deficient control group were fed with zinc-deficient feed and gavaged with an equal volume of normal saline; and the rats in normal control group were fed with control feed and gavaged with an equal volume of normal saline for two weeks.

3. Experimental results: During the feeding period, the reaction, activity, mental state, and hair changes of the rats were regularly observed, and the morphological changes of the rats were recorded by taking pictures. The feces of the rats were collected at the time of 24 h after the last intragastric administration, and then the rats were fasted at night. The rats were euthanized the next day, and their blood, livers, testes, kidneys, and pancreas were collected. The liver, testis, kidney, and pancreas tissues were snap-frozen in liquid nitrogen and preserved at −80° C. The blood samples were drawn into coagulation promoting tubes, and the serum was collected after centrifugation. The samples were frozen and preserved at −20° C. until analysis. The results showed that zinc deficiency negatively affects the growth and reproductive development of rat pups; due to differences in absorption and utilization, different zinc supplements have different recovery abilities to the body indicators; and the bioavailability of the zinc-enriched *B. animalis* CCFM1230 is higher than that of inorganic zinc, which can be better absorbed and utilized by organisms.

TABLE 5

Body lengths and widths of rats

| Group | Body length (cm) | Body width (cm) |
|---|---|---|
| Normal group | 20.33 ± 0.71$^{d}$ | 8.08 ± 0.41$^{c}$ |
| Zinc-deficient group | 15.45 ± 0.17$^{a}$ | 6.03 ± 0.15$^{a}$ |
| Inorganic zinc group | 19.33 ± 0.58$^{bc}$ | 7.7 ± 0.21$^{bc}$ |
| Zinc-enriched *B. animalis* group | 19.45 ± 0.24$^{bcd}$ | 7.85 ± 0.19$^{bc}$ |

Note:
Different letters represent significant differences between groups ($p < 0.05$)

TABLE 6

Testicular weights of rats

| Group | Testicular weight (g) |
|---|---|
| Normal group | 2.06 ± 0.09$^{d}$ |
| Zinc-deficient group | 1.45 ± 0.08$^{a}$ |
| Inorganic zinc group | 1.77 ± 0.09$^{bc}$ |
| Zinc-enriched *B. animalis* group | 2.05 ± 0.07$^{d}$ |

Note:
Different letters represent significant differences between groups ($p < 0.05$)

TABLE 7

Zinc content in rat tissues

| Group | Serum (μg/mL) | Liver (μg/g) | Testis (μg/g) | Pancreas (μg/g) | Kidney (μg/g) |
|---|---|---|---|---|---|
| Normal group | 5.68 ± 0.25$^{d}$ | 37.95 ± 2.31$^{c}$ | 22.48 ± 2.42$^{b}$ | 41.73 ± 4.79$^{d}$ | 26.89 ± 1.97$^{bc}$ |
| Zinc-deficient group | 4.23 ± 0.24$^{a}$ | 27.98 ± 1.79$^{a}$ | 14.68 ± 2.21$^{a}$ | 18.06 ± 1.40$^{a}$ | 22.13 ± 2.54$^{a}$ |

TABLE 7-continued

| Zinc content in rat tissues | | | | | |
|---|---|---|---|---|---|
| Group | Serum (μg/mL) | Liver (μg/g) | Testis (μg/g) | Pancreas (μg/g) | Kidney (μg/g) |
| Inorganic zinc group | 5.06 ± 0.13[b] | 27.98 ± 2.52[a] | 20.65 ± 0.48[b] | 19.43 ± 2.74[ab] | 24.72 ± 0.68[ab] |
| Zinc-enriched *B. animalis* group | 5.45 ± 0.17[cd] | 32.39 ± 2.41[abc] | 22.71 ± 0.62[b] | 31.96 ± 3.35[c] | 28.76 ± 0.76[c] |

Although the present disclosure has been disclosed as above in exemplary examples, it is not intended to limit the present disclosure. Anyone familiar with this technology can make various changes and modifications without departing from the spirit and scope of the present disclosure. Therefore, the protection scope of the present disclosure shall be as defined in the claims.

What is claimed is:

1. A freeze-dried probiotic preparation, comprising: a) *Bifidobacterium animalis* (*B. animalis*) CCFM1230 cells, b) cell lysates of the *B. animalis* CCFM1230, or c) a combination of a) and b), wherein the *B. animalis* CCFM1230 has been subjected to zinc enrichment culture, which comprises:

culturing the *B. animalis* CCFM1230 to produce a seed bacterial liquid, inoculating the seed bacterial liquid into a liquid medium comprising zinc, and culturing the seed bacterial liquid to produce a zinc-rich *B. animalis* CCFM1230 fermentation product, centrifuging the zinc-rich *B. animalis* CCFM1230 fermentation product, rinsing the zinc-rich *B. animalis* CCFM1230 fermentation product, mixing the zinc-rich *B. animalis* CCFM1230 fermentation product with skimmed milk having a mass fraction of 13% (w/w), and freeze-drying the zinc-rich *B. animalis* CCFM1230 fermentation product, wherein the *B. animalis* CCFM1230 has been preserved in Guangdong Microbial Culture Collection Center (GDMCC) on Feb. 11, 2022, with a preservation number of GDMCC No: 62248, and wherein the zinc-rich *B. animalis* CCFM1230 fermentation product comprises 200 to 700 mg/L zinc ion.

2. The freeze-dried probiotic preparation according to claim 1, wherein the *B. animalis* CCFM1230 cells comprise living cells or dead cells.

3. The freeze-dried probiotic preparation according to claim 2, wherein the dead cells comprise naturally inactive cells or inactivated cells.

4. The freeze-dried probiotic preparation according to claim 3, wherein the freeze-dried probiotic preparation comprises an amount of at least $1\times10^{10}$ CFU/g or CFU/mL of the *B. animalis* CCFM1230 cells.

5. The freeze-dried probiotic preparation according to claim 4, wherein culturing the zinc-rich *B. animalis* CCFM1230 fermentation product is performed until the number of the *B. animalis* CCFM1230 cells in the preparation is greater than or equal to $1\times10^{8}$ CFU/mL.

6. The freeze-dried probiotic preparation according to claim 1, wherein the freeze-drying comprises vacuum freeze drying.

7. The freeze-dried probiotic preparation according to claim 1, wherein the liquid medium comprises:

20 g/L to 30 g/L glucose,
15 g/L to 25 g/L nitrogen source,
2 g/L anhydrous sodium acetate,
2 g/L diammonium hydrogen citrate,
2.6 g/L $K_2HPO_4\cdot3H_2O$,
0.1 g/L $MgSO_4\cdot7H_2O$,
0.05 g/L $MnSO_4\cdot H_2O$,
1 g/L Tween-80,
0.5 g/L cysteine, and
zinc sulfate.

8. The freeze-dried probiotic preparation according to claim 7, wherein the nitrogen source comprises yeast extract powder and peptone at a mass ratio of 1:2.

9. The freeze-dried probiotic preparation according to claim 1, wherein the zinc-enriched *B. animalis* CCFM1230 fermentation product is inactivated before the freeze-drying.

10. A method of promoting the growth and reproductive development of young mammals, which comprises:

administering to the mammals a probiotic preparation, comprising: a) *Bifidobacterium animalis* (*B. animalis*) CCFM1230 cells, b) cell lysates of the *B. animalis* CCFM1230, or c) a combination of a) and b), wherein the *B. animalis* CCFM1230 has been subjected to zinc enrichment culture, which comprises:

culturing the *B. animalis* CCFM1230 to produce a seed bacterial liquid, inoculating the seed bacterial liquid into a liquid medium comprising zinc, and culturing the seed bacterial liquid to produce a zinc-rich *B. animalis* CCFM1230 fermentation product, centrifuging the zinc-rich *B. animalis* CCFM1230 fermentation product, rinsing the zinc-rich *B. animalis* CCFM1230 fermentation product, mixing the zinc-rich *B. animalis* CCFM1230 fermentation product with skimmed milk having a mass fraction of 13% (w/w), and freeze-drying the zinc-rich *B. animalis* CCFM1230 fermentation product, wherein the *B. animalis* CCFM1230 has been preserved in Guangdong Microbial Culture Collection Center (GDMCC) on Feb. 11, 2022, with a preservation number of GDMCC No: 62248, and wherein the zinc-rich *B. animalis* CCFM1230 fermentation product comprises 200 to 700 mg/L zinc ion.

11. The method according to claim 10, wherein the probiotic preparation is a food, a medicine, or a health care product.

12. A freeze-dried probiotic preparation, comprising:

*Bifidobacterium animalis* (*B. animalis*) CCFM1230 or a cell lysate thereof, organic zinc, skimmed milk as a protective agent, wherein the *B. animalis* CCFM1230 has been preserved in Guangdong Microbial Culture Collection Center (GDMCC) on Feb. 11, 2022, with a preservation number of GDMCC No: 62248.

13. The freeze-dried probiotic preparation of claim 12, wherein the preparation comprises 200 to 700 mg/L of the organic zinc.

14. The freeze-dried probiotic preparation of claim 12, wherein the *B. animalis* CCFM1230 has been subjected to zinc-enrichment culturing, which comprises:

culturing the *B. animalis* CCFM1230 to produce a seed bacterial liquid, inoculating the seed bacterial liquid into a liquid medium comprising zinc, and culturing the seed bacterial liquid to produce a zinc-rich *B. animalis* CCFM1230 fermentation product, centrifuging the zinc-rich *B. animalis* CCFM1230 fermentation product, rinsing the zinc-rich *B. animalis* CCFM1230 fermentation product, mixing the zinc-rich *B. animalis* CCFM1230 fermentation product with skimmed milk having a mass fraction of 13% (w/w), and freeze-drying the zinc-rich *B. animalis* CCFM1230 fermentation product.

15. The freeze-dried probiotic preparation of claim 12, wherein the freeze-dried preparation comprises only the cell lysate.

* * * * *